(12) United States Patent
Trefz

(10) Patent No.: US 8,432,276 B2
(45) Date of Patent: Apr. 30, 2013

(54) SYSTEM AND APPARATUS FOR ALERTING A USER IN RESPONSE TO ENVIRONMENTAL CONDITIONS

(76) Inventor: Elmar Trefz, Sindelfingen (DE)

( * ) Notice: Subject to any disclaimer, the term of this patent is extended or adjusted under 35 U.S.C. 154(b) by 843 days.

(21) Appl. No.: 11/658,953

(22) PCT Filed: Jun. 23, 2005

(86) PCT No.: PCT/AU2005/000912
§ 371 (c)(1),
(2), (4) Date: May 27, 2009

(87) PCT Pub. No.: WO2006/010197
PCT Pub. Date: Feb. 2, 2006

(65) Prior Publication Data
US 2010/0066533 A1 Mar. 18, 2010

(30) Foreign Application Priority Data
Jul. 30, 2004 (AU) ................................ 2004904300

(51) Int. Cl.
*G08B 21/00* (2006.01)
(52) U.S. Cl.
USPC ................... 340/540; 340/407.1; 340/539.26
(58) Field of Classification Search .................. 340/540, 340/309.16, 407.1, 539.26, 539.27, 539.28, 340/539.29, 573.1, 575; 381/301, 388; 5/636, 5/637, 639, 640
See application file for complete search history.

(56) References Cited

U.S. PATENT DOCUMENTS

| | | | | |
|---|---|---|---|---|
| 5,144,600 | A * | 9/1992 | Cheng | 368/12 |
| 5,686,884 | A * | 11/1997 | Larkin et al. | 340/506 |
| 6,307,751 | B1 | 10/2001 | Bodony et al. | |
| 7,177,859 | B2 * | 2/2007 | Pather et al. | 1/1 |
| 7,461,422 | B1 * | 12/2008 | Baker | 5/639 |
| 7,484,255 | B2 * | 2/2009 | Ho | 5/636 |
| 7,540,847 | B2 * | 6/2009 | Klein et al. | 601/46 |
| 2004/0039254 | A1 | 2/2004 | Stivoric et al. | |
| 2004/0222879 | A1 * | 11/2004 | Sawyer et al. | 340/407.1 |

FOREIGN PATENT DOCUMENTS

| | | |
|---|---|---|
| DE | 20302102 | 8/2003 |
| EP | 0317230 | 3/1995 |
| GB | 2376115 | 12/2002 |

* cited by examiner

*Primary Examiner* — Toan N Pham
(74) *Attorney, Agent, or Firm* — Olson & Cepuritis, Ltd.

(57) ABSTRACT

An apparatus and system 10,10',10" for alerting a user to an environmental condition comprises a stimulus means 18,20, 22 positionable with respect to the user so as to stimulate the user in a tactile manner in response to a predetermined environmental condition.

24 Claims, 4 Drawing Sheets

SYSTEM AND APPARATUS FOR ALERTING A USER IN RESPONSE TO ENVIRONMENTAL CONDITIONS

CROSS-REFERENCE TO RELATED APPLICATIONS

This application is the U.S. National Stage of International Application No. PCT/AU2005/000912, filed Jun. 23, 2005 the disclosures of which are incorporated herein by reference.

TECHNICAL FIELD

A system and apparatus for alerting (eg. waking) a user in response to certain (eg. predetermined) environmental conditions is disclosed. The environmental conditions can, for example, be conditions of a physical environment (eg. weather) or of a man-made environment a stock market).

BACKGROUND ART

Computer programs are known for providing an alert to a user when a certain predetermined environmental condition is reached. For example, programs are known that monitor and alert users to changes in a given parameter (eg. movement on the stock market, or a certain change in a stock price, commodity price change etc). The alert may be provided to the user in the form of an electronic mail, wireless short message or an audible alarm.

SUMMARY

In a first aspect there is provided apparatus for alerting a user to an environmental condition, the apparatus comprising stimulus means positionable with respect to the user so as to stimulate the user in a tactile manner in response to a predetermined environmental condition.

By providing a stimulus means that stimulates a user in a tactile manner, a more reliable or more readily user-detected way of alerting the user is provided. For example, the stimulus means can be used to wake a user from sleep, thereby alerting that user to the occurrence of the predetermined environmental condition. The stimulus means may also be used to alert sight and/or hearing impaired users.

In one embodiment the stimulus means is incorporated within a flexible housing that is positionable adjacent to the user. The flexible housing may form part of a pillow, cushion, pad etc that can be positioned adjacent to a part of the user's anatomy. The pad may optionally form part of a user's clothing.

In one embodiment, the stimulus means comprises an actuator eg. located in the housing. For example, the actuator can be of a mechanical type (eg. electro-mechanical) and may comprise an eccentric or cammed mass that is driven (eg. rotated) by a motor to cause vibration. The mass may be disposed on a rotor shaft of the motor, so that when the shaft is rotated the mass sets up a vibration within the actuator. The vibration thus provides a tactile-type stimulus in the apparatus. The motor may be in electrical or remote connection with a switching device for selective actuation thereof (eg. in response to a monitored environmental condition).

The switching device may further comprise a controller/transformer for controlling the motor in response to a signal, and/or transforming the signal into electrical power for the motor, with the signal being related to the monitored environmental condition. In this regard, the switching device may comprise a microprocessor as controller.

The signal may emanate from a variety of sources and may be transmitted via hard wire, or wirelessly to the controller/transformer. For example, the signal may be transmitted from a computer using eg. RF modules at the computer and at the controller. In another embodiment the signal may be transmitted from a base station using emf radiation (eg. radio, a mobile telecommunication signal, infrared, microwave etc).

Other actuators can be employed. For example, alternative vibrating type devices, or actuators that release a mild electrical charge, a vibration-causing noise etc, may be employed.

In a second aspect there is provided a system for alerting a user to an environmental condition, the system comprising:
 monitoring means for monitoring for a predetermined environmental condition; and
 stimulus means for stimulating the user in a tactile manner in response to the predetermined environmental condition monitored by the monitoring means.

In a third aspect there is provided a system for alerting a user to an environmental condition, the system comprising:
 monitoring means for monitoring for a predetermined environmental condition; and
 stimulus means for stimulating the user in response to the predetermined environmental condition monitored by the monitoring means;
 wherein the stimulus means is other than a speaker, graphical user interface, or a computer.

The term "graphical user interface" is to be interpreted broadly herein to include screens or the like associated with computers, mobile phones, hand held and portable computers and organisers, pagers etc. Again, the term "computer" is to be interpreted broadly herein to include: desktop computers, laptop computers, hand held and other portable computers and organisers, mobile phones, pagers etc; and whether stand-alone or part of a network etc.

In the system defined in the second and third aspects, the stimulus means is typically as defined in the first aspect. In this regard, the system may employ the apparatus of the first aspect.

In the system defined in the second and third aspects, the monitoring means can comprise a computer program stored on or otherwise associated with or accessible by a computer (eg. over a network). In this regard, the computer program can be configured to read information from the computer, or read or receive it from a network to which the computer is connected. The information is typically indicative of the environmental condition and, when the predetermined environmental condition is reached, the computer program can be configured to prompt and thus generate a signal to be sent to the stimulus means.

The network can be a restricted user network (such as an intranet, local area network etc) or may be a global user network (such as the Internet). The information may be stored on a site or host computer accessible via the network.

The predetermined environmental condition may be selected or determined by the user, or by the site or host computer (eg. by an operator at the site or host computer), or by the computer program. The predetermined environmental condition can be one or a number of conditions and may be defined by one or a number of parameters.

In the system the signal provided to the stimulus means may be sent from the computer to the stimulus means electrically, electronically or remotely (eg. by wireless means). In the system the signal provided to the stimulus means may also be sent via a microprocessor controller that is adapted to translate/transform the signal so that it is useable to activate the stimulus means. For example, where the stimulus means comprises a motor or other electrically activatable device (eg.

a vibrating device or the like) the microprocessor can act as either or both of switch, or controller (ie. to activate/deactivate the motor or other device) or transformer to provide appropriate voltage and current to the motor or other device.

In the system of the third aspect (ie. when the stimulus means is other than a speaker, a graphical user interface, or a computer), the stimulus means may operate other than in a tactile manner, and may stimulate other senses of a user, such as sight, taste or smell.

In a typical embodiment of the system the stimulus means is separate from but is activated responsive to the monitoring means once it monitors the predetermined environmental condition. In this regard, the stimulus means may also comprise a device that releases to a user a light signal, or a detectable odour or flavour.

The predetermined environmental condition can be a condition of a physical environment or of a man-made environment. For example, the physical environmental conditions are especially those that are variable. These physical environmental conditions may include: weather conditions, conditions of water bodies, surf conditions, fishing conditions, water temperature (eg. of seas, lakes or rivers), air temperature, wind conditions, snow or rain conditions, etc. These conditions may be relevant to users playing sport or undertaking hobbies or outings in such conditions.

The man-made environment conditions are also especially those that are variable. These man-made environmental conditions may include conditions or states of: stock and other markets, individual or group stock price(s), commodity goods or services price(s), interest rates, foreign exchange rates, property prices, etc. These conditions may be relevant to users working with or personally interested in such conditions.

BRIEF DESCRIPTION OF THE DRAWINGS

Notwithstanding other embodiments which may incorporate some or all of the features as outlined in the Summary, a number of specific system and apparatus embodiments will now be described, by way of example only, with reference to the Examples and the accompanying drawings in which.

DETAILED DESCRIPTION OF SPECIFIC EMBODIMENTS

Figure 1:
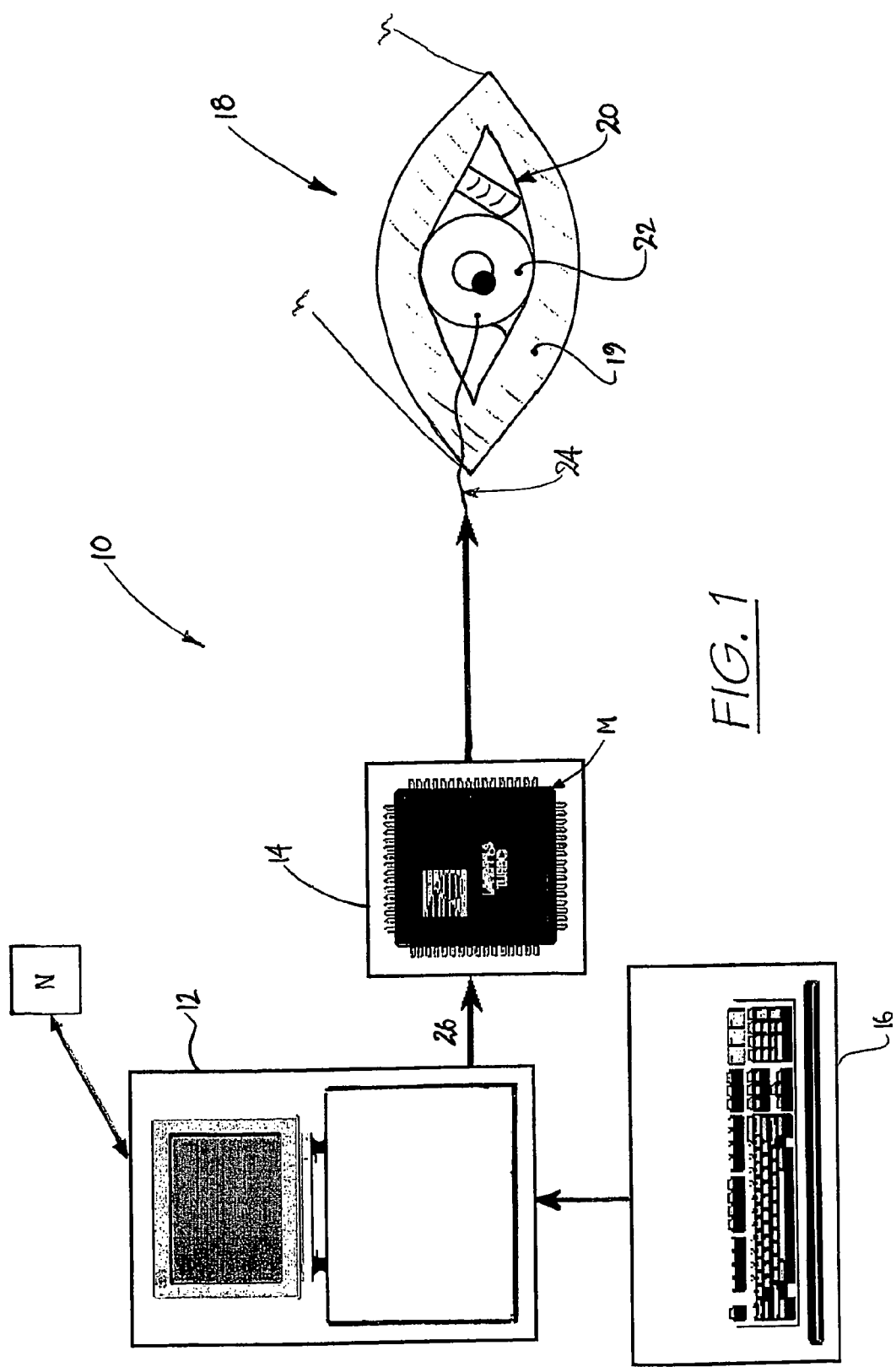
FIG. 1 schematically depicts a first system and apparatus embodiment.
Figure 2:
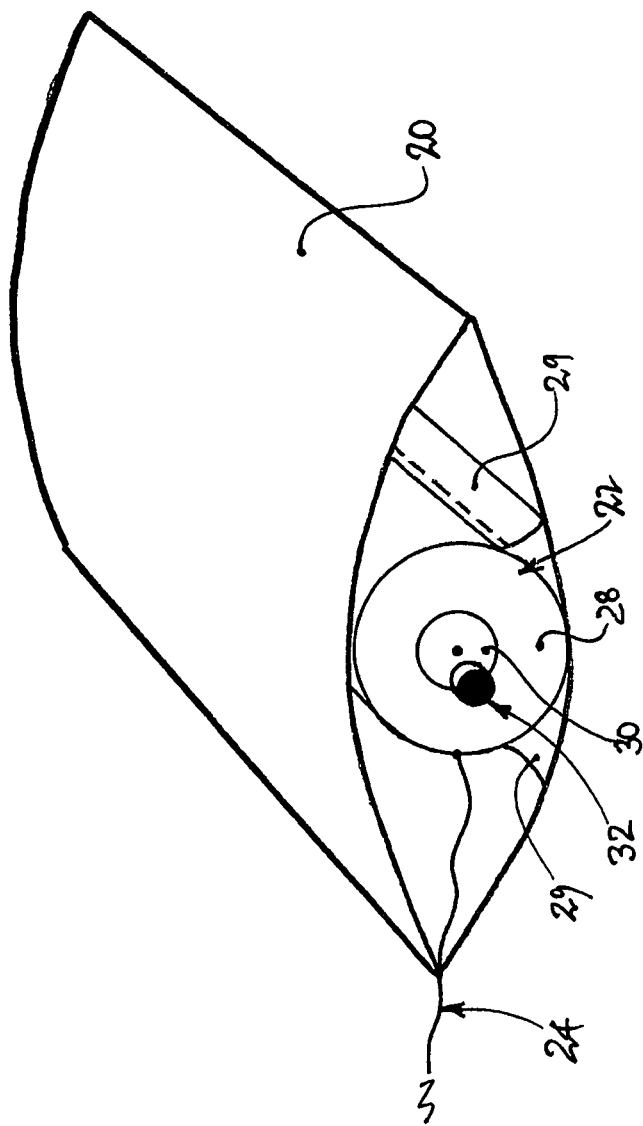
FIG. 2 shows a cross-sectional view through part of the apparatus of FIG. 1.

Referring firstly to FIGS. 1 and 2, where like reference numerals are used to denote similar or like parts, a system and apparatus for alerting a user to an environmental condition is schematically depicted. The system 10 comprises a computer 12 and a controller 14. The controller typically incorporates a microprocessor M to provide it with some intelligence and programmable capacity.

Data, commands and/or instructions may be entered into the computer via an input module 16 (eg. a keyboard). The computer 12 is typically in communication with a network N which may comprise a restricted user network (such as an intranet, local area network etc) or a global user network (such as the Internet).

Apparatus for alerting a user to an environmental condition and comprising a stimulus device is shown in the form of a cushion or pillow 18 in FIG. 1. Housed within the cushion or pillow 18 is padding 19. The padding surrounds a stimulus device comprising a casing 20 and an actuator in the form of a motor 22. The motor 22 is in electrical or remote (eg. wireless) connection with the controller 14, for example via a wire schematically depicted as 24. The controller 14 may also be housed within the casing 20 (see FIG. 4).

The wire 24 may simply communicate an on/off switching function to motor 22 (which may have its own power source—eg. battery) and/or the wire may supply power from the controller 14. In this regard, controller 14 itself may simply act as a switching device responsive to a signal 26 from the computer 12. The controller 14 may additionally or alternatively comprise a transformer/power supply for ramping up the signal, or for directing power responsive to the signal, to the motor 22. In this regard, the controller can supply the appropriate voltage and current to the motor 22 to actuate the same.

Referring particularly to FIG. 2, stimulus means forming part of the apparatus for alerting a user to an environmental condition is shown as comprising the casing 20 which is typically formed from a flexible (eg. plastics) yet protective material. The motor 22 is positioned within the casing and comprises a stator portion 28 mounted to the casing via bearings 29. A rotor portion 30, defining an elongate shaft, is mounted to be rotationally driven within the stator portion.

Typically opposite ends of the rotor portion 30 are each mounted with a respective cylindrical mass 32, each mass being offset from a centre of the rotor portion 30 as shown (or alternatively being movable by a cam). Thus, when the motor is actuated and the rotor is rotated at speed, the offset mass (or cam) causes the motor and thus the casing 20 to vibrate, thereby providing a vibrational output that may be sensed by a user of the cushion or pillow 18. In this regard, the vibrational forces are transmitted through the padding 19 and thence into that portion of the user's anatomy positioned on or adjacent to the cushion or pillow 18. This can alert the user (eg. by waking them).

In a further variation a pressure activated switch can be built into the casing 20 which is activated when pressure is placed onto the pillow and thence the casing by a user lying or otherwise pressing onto the pillow. Usually this pressure closes a circuit, which then feeds power to the motor. Such an arrangement can then allow the pillow to be utilised all day so that, should the environmental conditions prevail at any time during the day, the pillow is only caused to vibrate when a user places pressure on it. In other words, this provides an on/off switch built into the pillow itself. In a simple form the switch can be defined in a circuit connected to two contacts between eg. an interior wall of the casing and an exterior wall of the motor, whereby pressure, placed on the pillow urges the casing against the motor and thence closes the circuit.

Figure 4:
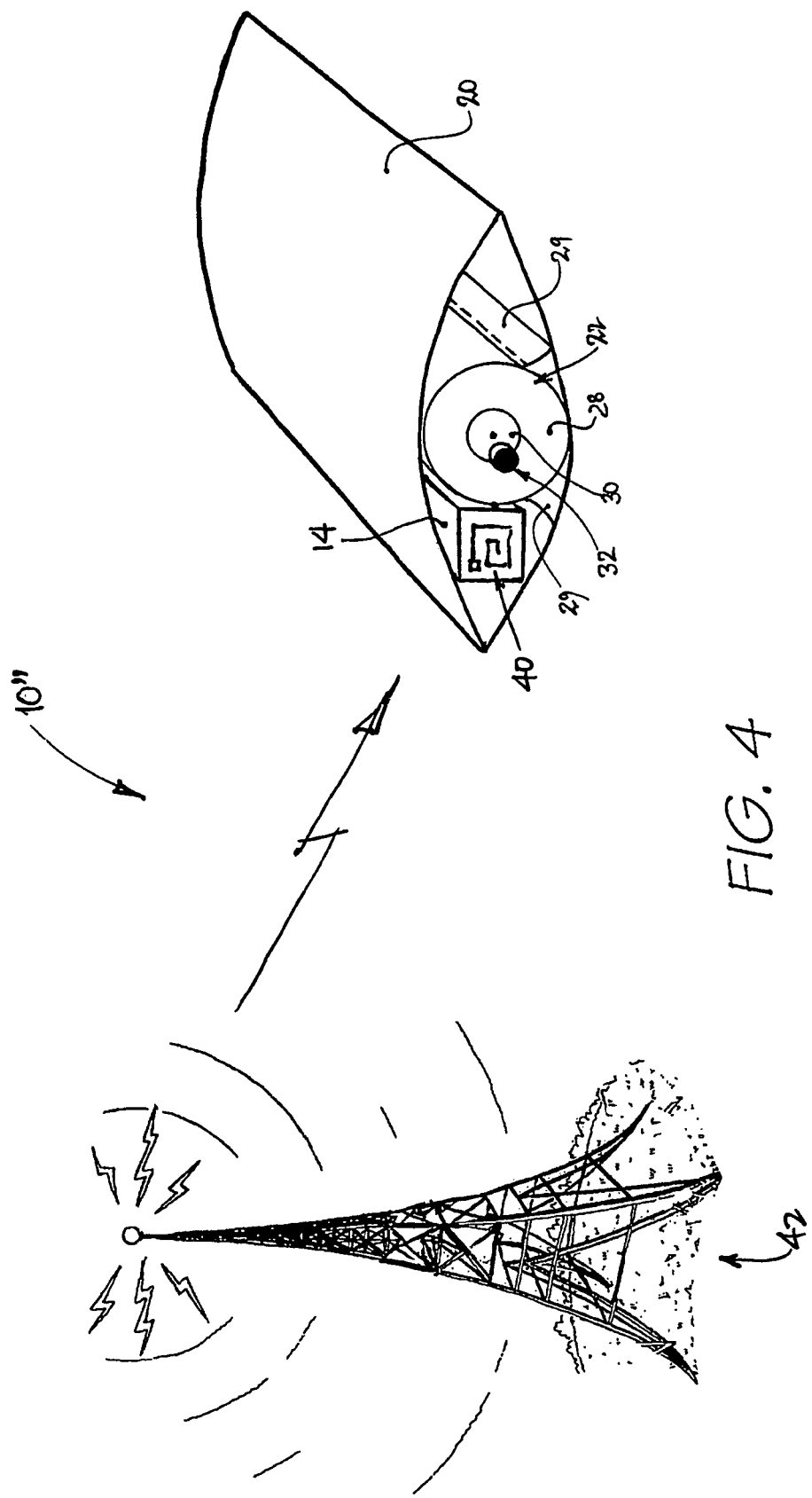
FIG. 4 schematically depicts a third system and apparatus embodiment.

The pillow can be remotely connected to the computer, or it may be connected to a telephony or other type of communications network via eg. an SMS or similar type receiver within the casing or pillow construction interior. In one example, a signal may be transmitted from a computer using RF modules at the computer and at the controller. In another example, the signal may be transmitted from a base station (see eg. FIG. 4) using emf radiation (eg. radio, a mobile telecommunication signal, infrared, microwave etc).

There is thus no need for a computer in the user's residence or in the vicinity of the pillow. Rather, the pillow vibration can be turned on and off via a signal sent from a network when certain (eg. predetermined) environmental conditions are reached. In this regard, the pillow may also comprise a microprocessor within the casing (or similar interior construction) of the pillow, so that multiple different control communication possibilities can be provided for in the one set-up, including wireless, SMS and other emf-type communication.

In addition, the motor can be controlled to rotate at differing speeds which can relate to a proportion or magnitude of one or more of the parameters associated with the environmental conditions. For example, where the environmental condition being monitored is surf condition, the degree of vibration can be related to the size of the waves. In this regard, a small wave height can produce a small vibration, whereas a large wave height can produce a large vibration. A similar vibrational or tactile variability can also be employed with other stimulus means embodiments, including the embodiments now described with reference to FIGS. 3 and 4.

Figure 3:
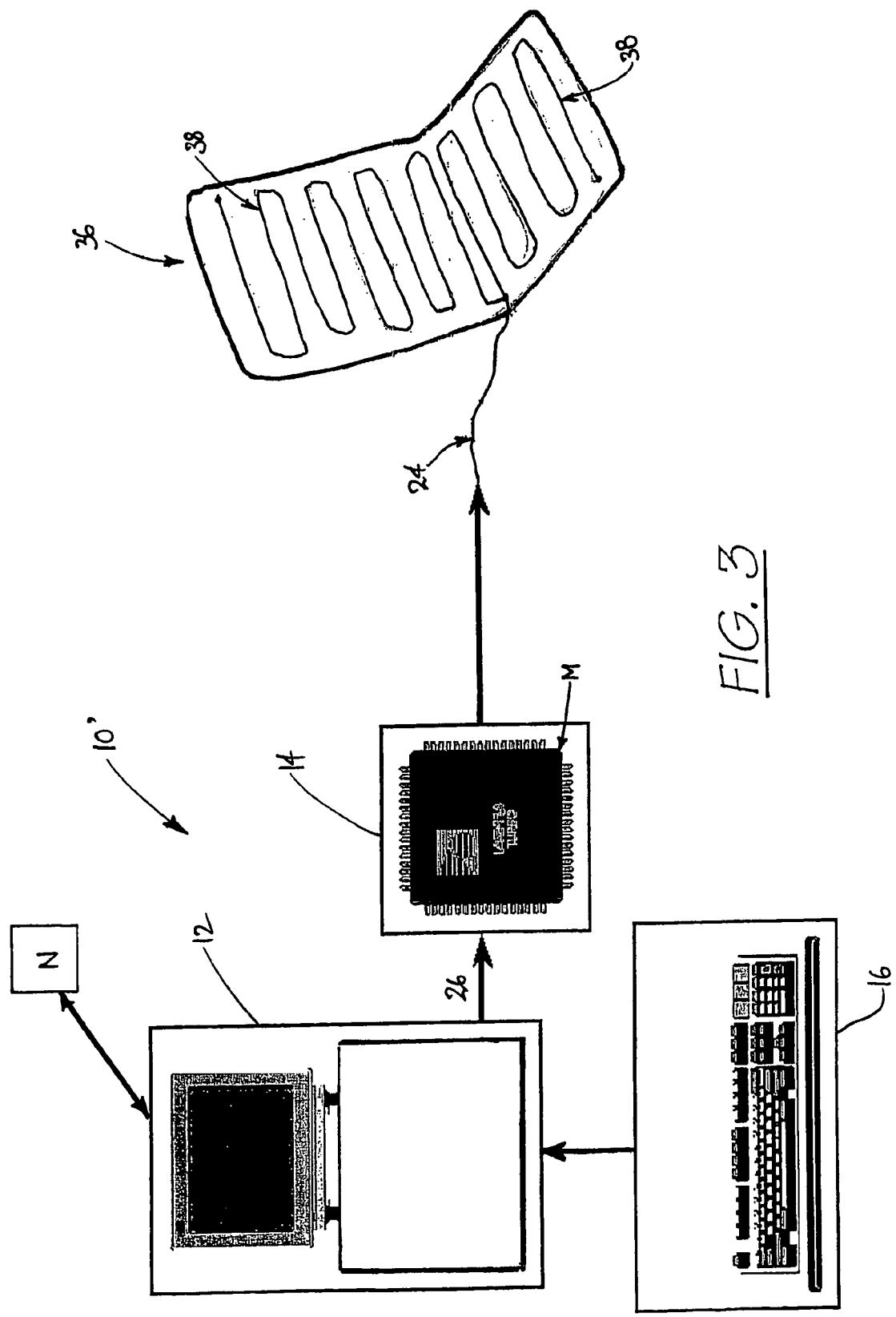
FIG. 3 schematically depicts a second system and apparatus embodiment.

Referring firstly to FIG. 3, where like reference numerals are used to denote similar or like parts, an alternative system and apparatus for alerting a user to an environmental condition is schematically depicted. In this system 10', in place of cushion or pillow 18, a chair-shaped enlarged support pad 36 is depicted. Mounted to extend within support pad 36 is an elongate element 38, the element being connected to the controller 14 via wire 24 (or alternatively remotely connected thereto, such as by wireless communication—in which case the element 38 has its own power supply). The elongate element may be configured to vibrate in response to an electric current passed therethrough or may be configured to heat up (ie. by having an electrical resistance). In both cases the element provides tactile stimulation to a user positioned thereon (eg. seated thereon). In this regard, the support pad may be positioned on a chair at which the user normally sits (eg. a work or office chair). In other respects the system 10' is as described for the system 10 of FIGS. 1 and 2.

Referring now to FIG. 4, where like reference numerals are used to denote similar or like parts, a further alternative system and apparatus for alerting a user to an environmental condition is schematically depicted. In this system 10" the controller 14 is positioned inside the casing 20 and includes a generally flat receiver aerial 40. That aerial is adapted to receive a signal transmitted remotely from a base station antenna 42. The signal is sent responsive to the detection of a predetermined environmental condition in a network of which the antenna is a part. In other respects the system 10" is as described for the system 10 of FIGS. 1 and 2.

The systems of FIGS. 1 to 4 may be operated as follows. Firstly, a computer program can be loaded onto the computer 12. The program is typically configured to analyse, interpret and utilise information on and from the network N. The computer program may also receive user information and data via input module 16.

Information on the network N that is accessed by the computer program typically relates to some type of environmental condition, especially of a variable nature. For example, the environmental conditions may be conditions pertaining to the physical environment, such as weather conditions, water body conditions, surf conditions, fishing conditions, water (eg. sea, lake or river) temperature, air temperature, wind conditions, snow or rain conditions, road conditions, airport or airstrip conditions etc. Alternatively, they may be man-made environmental conditions such as the condition or states of: stock and other markets, individual or group stock price(s), commodity goods or services price(s), interest rates, foreign exchange rates, property prices etc.

The computer program is programmed to interrogate such information and monitor variations in the parameters (or metrics) which record and measure changes in such environmental conditions. A user may, via the input module, indicate that when certain perimeters reach certain values or fall within certain ranges, they would like to be alerted via one or more of the various stimulus means described above and herein. In this regard, once one or more of those parameters are reached or realised, the computer 12 is caused by the computer program to generate a signal 26 to the controller 14, which then processes that signal and sends out an activation command either via the wire 24 or remotely (eg. via a wireless protocol) to the motor 22 or to the element 38.

The actuation of the motor 22 or the wire 38 ultimately stimulates the user through the sense of touch and thereby alerts them to a change in the environmental condition. That change may be something that the user has predetermined, something that the program predetermines or that is predetermined by instructions received from the network. For example, another site on the network may need to alert one or more users of a change in user-relevant environmental conditions and may thereby communicate to users using the system 10.

A number of non-limiting Examples will now be described.

EXAMPLE 1

A user of the system 10 of FIGS. 1 and 2 wishes to be alerted of surf conditions decided by that user to be optimal. In this regard, a purpose-built program is loaded onto computer 12 and that program communicates with one or more websites via the Internet.

In this particular Example, one website on the Internet is dedicated to providing weather conditions that pertain to surf conditions in various surf locations that are accessible by the user. The user activates the computer program and, via input module 16, enters values or ranges for various parameters into the computer program as follows:

Wave Height; Wind Direction; Wave (Swell) Period; Water Temperature; Air Temperature; Tide Height.

The user then specifies that when the values for each of these parameters reach a certain value or fall within certain ranges, the program is to then provide an alert signal, which is signal 26. When provided, this signal is then fed via controller 14 through to the motor 22.

In this Example, the user wishes to be woken from sleep, and thus makes use of the cushion or pillow 18. Thus, when the signal is fed to the motor 22, it causes the user's pillow to vibrate and wake the user. Further, in this Example, the user specifies that pillow vibration is only to occur at a time starting from half an hour prior to sunrise onwards, and should those parameters reach the certain values, the pillow 18 is then to be activated. The user then sleeps on this pillow with their head resting thereagainst, with the knowledge that when the pillow 18 vibrates, and they are woken, that optimal surf conditions exist. In this way, the user may sleep normally and comfortably, and then be woken as desired, without ever having to monitor those conditions otherwise.

Alternatively or additionally, the user makes use of pad 36 and, should the parameters reach a certain value or fall within certain ranges at a certain time of the day, the element 38 is activated.

EXAMPLE 2

In this example, the user makes use of the system of FIG. 3. In this example, the user is concerned with monitoring the value of a particular stock on the stock market, and the computer program is configured to monitor and interrogate prices of that stock as listed on the stock exchange, via a stock exchange's website.

The user wishes to be notified whilst at work, and hence the support pad 36 is positioned on the user's work chair. The user then enters value(s) into the computer program housed on the user's work computer, which is connected to the Internet.

In this Example the user, via input module 16, determines a value range for the stock price in which the user wishes to be notified when that range is reached. The user then continues to work in the usual manner, but when the stock reaches that value the user is stimulated in a tactile manner via the vibration (or heating) of elements 38 within pad 36.

In this Example, the user can either supplement or no longer rely on alert programs that message or audibly notify the user. The user may now turn off any speakers or turn down the volume on his/her computer because the user will be notified of any change through touch.

The use of a touch alert is also useful in busy or noisy environments (eg. stock markets are notoriously noisy), or where the user is visually or hearing impaired.

EXAMPLE 3

In this example, the user makes use of a system which is a modification of the system shown in FIG. 3. In this regard, the controller 14 and support pad 36 are configured together in a unit, and units are now attached within the lining of each of a user's jackets.

The user has a hand held computer and that computer is programmed to periodically log onto and access the Internet via a wireless access protocol (eg. using the Blue Tooth™ protocol). The hand held computer also outputs a signal 26 via the wireless access (Blue Tooth™) protocol, which is received via the controller 14, also set up with a wireless (Blue Tooth™) protocol.

A power supply is provided with the controller (eg. a battery) and that provides power to activate a vibration device within the pad 36, causing tactile stimulation of that part of the user's anatomy adjacent to the pad 36. In this regard, the user can be provided with the tactile stimulation whilst they are mobile and hence the system 10 can be portable.

In this Example, a standard format or protocol for accessing and interacting with any of a number of websites of different environmental condition content can be provided. Each website may subscribe to the protocol. For example, the hand held computer may only need to carry one generalised computer program, and the user can then point the program at a given website, select the parameters they want monitored and select when they want to be notified.

EXAMPLE 4

In this example, the user makes use of a system which is as shown in FIG. 4. In this regard, the casing 20 can be of a size to be carried by the user and/or may form part of the user's personal digital assistant (PDA) or similar device. The unit can also be carried in or clipped onto a user's clothing.

The controller 14 is now operational at all times and can receive a specified signal type whenever in the vicinity of an antenna 42.

In this example, a power supply is provided within the casing and provides power to the controller, the aerial and to activate the motor to cause tactile stimulation of that part of the user's anatomy adjacent to the casing or device. Thus, the user can be provided with the tactile stimulation whilst they are mobile so that again the system 10" is portable.

In this particular Example, a telecommunications service provider is dedicated to providing weather conditions that pertain to snow conditions in various locations that are accessible by the user. The user activates a service (eg. via mobile phone or PDA) and, via phone or PDA, enters one or more values or ranges for various parameters into the website as follows:

Snow Depth; Snow Freshness; Snow Quality (ie. degree of powder); Air Temperature; Wind; Weather parameters; Avalanche Risk.

Many other variations of the embodiments described above are possible, as would be understood by a person skilled in the art.

The computer 12 may be any type of "computer" as defined above in the Summary section. Similarly, the controller 14 may be a simple microprocessor or may comprise a microprocessor in conjunction with a transformer and power supply, and may then directly provide the power supply to the motor 22 or element 38. The input module 16, whilst shown as a keyboard, may equally be replaced by any device which enables input into a "computer" including a mobile phone, portable or handheld computer, or even a voice-activated input module.

The various stimulation means described are indicative only, and it is conceivable that other user senses could be stimulated via other means. For example, stimulus means could be configured to release an odour when activated via the controller 14, or to release a flavour that could be tasted by a user (eg. via a straw or the like). The stimulus means may also be a separate stand-alone light-emitting device which could flash or illuminate in a highly eye-catching manner.

The predetermined environmental condition can be one or a number of conditions and may be defined by one or a number of parameters.

The cushions, pads, pillows etc can be formed from lightweight yet supportive and strong materials. Typically many of the components are formed from structural polymeric material to minimise weight and also to enable ease of manufacture (eg. via moulding, and machine weaving).

The system and apparatus embodiments described herein can be embodied in many other forms.

The invention claimed is:

1. An apparatus for alerting a user to an environmental condition predetermined by the user, the environmental condition defined by at least one user-selected variable parameter relating to the environmental condition and being imparted to the apparatus by accessing and interrogating information maintained on an associated network relating to the at least one variable parameter, the apparatus comprising:
    a stimulus device incorporated within a flexible housing forming a part of a pillow, cushion or pad that is positionable with respect to the user and adapted for actuation so as to alert the user in a tactile manner in response to the at least one user-selected variable parameter reaching a value of the defined environmental condition predetermined by the user.

2. The apparatus of claim 1 wherein the flexible housing is positionable adjacent to the user.

3. The apparatus of claim 1 wherein the pillow, cushion or pad is adapted to be utilized in conjunction with a bed or chair.

4. The apparatus of claim 1 wherein the pillow, cushion or pad forms part of a user's clothing.

5. The apparatus of claim 1 wherein the stimulus device comprises an actuator located within the housing.

6. The apparatus of claim 5 wherein the actuator is electromechanical.

7. The apparatus of claim 6 wherein the actuator comprises a motor, and an eccentric or cammed mass that is disposed on a rotor shaft of the motor to be driven thereby, such that, when the shaft is rotated, the mass sets up a vibration within the actuator, the vibration thereby providing a tactile-type stimulus in the apparatus.

8. The apparatus of claim 7 further comprising a switching device, wherein the motor is in electrical or remote connection with the switching device for selective actuation of the motor in response to a monitored environmental condition.

9. The apparatus of claim 8 wherein the switching device further comprises a controller/transformer for controlling the motor in response to a signal, or transforming the signal into electrical power for the motor, or both, the signal being related to the monitored environmental condition.

10. The apparatus of claim 9 wherein the signal is transmitted via hard wire, or wirelessly to the controller/transformer.

11. The apparatus of claim 10 wherein the signal is wirelessly transmitted from a computer using RF modules at the computer and at the controller, or is transmitted from a base station using emf radiation including radio, a mobile telecommunication signal, infrared, or microwave radiation.

12. A system of alerting a user to a predetermined environmental condition defined by at least one variable parameter predetermined by the user, the system comprising:
   a monitoring device adapted for accessing and interrogating information maintained on an associated network relating to the at least one variable parameter;
   a stimulus device incorporated within a flexible housing that is positionable with respect to the user and adapted for actuation so as to alert the user in a tactile manner; wherein the monitoring device is adapted to cause actuation of the stimulus device in accordance with the at least one variable parameter attaining a predetermined value; and
   an input module in communication with the monitoring device and adapted for receiving user input relating to the environmental condition predetermined by the user.

13. The system of claim 12 wherein the housing of the stimulus device forms part of a pillow, cushion or pad.

14. The system of claim 12 wherein the monitoring device comprises a computer program stored on or otherwise associated with or accessible by a computer.

15. The system of claim 14 wherein the computer program is configured to read information from the computer, or read or receive it from a network to which the computer is connected, the information being indicative of the environmental condition such that, when the predetermined environmental condition is reached, the computer program provides a signal to the stimulus device.

16. The system of claim 15 wherein the network is a restricted user network or is a global user network.

17. The system of claim 15 wherein the information may be stored on a site or host computer accessible via the network.

18. The system of claim 17 wherein the predetermined environmental condition is selected or determined by the user, or by the site or host computer, or by the computer program.

19. The system of claim 15 wherein the signal provided to the stimulus device is sent from the computer electrically, electronically or remotely.

20. The system of claim 15 wherein the signal provided to the stimulus device is sent via a microprocessor that is adapted to translate/transform the signal so that it is useable by the stimulus device.

21. The system of claim 20 wherein, when the stimulus device comprises a motor or other electrically activatable device, the microprocessor acts as either a switch, or a transformer, or as both, to provide appropriate voltage and current, to the motor or other device.

22. The system of claim 12 wherein the predetermined environmental condition is a condition of a physical environment or of a man-made environment.

23. The system of claim 22 wherein the environmental conditions are variable, the physical environmental conditions being selected from the group consisting of weather conditions, surf conditions, fishing conditions, water body conditions, water temperature, air temperature, wind conditions, and snow or rain conditions; and the man-made environmental conditions being selected from the group consisting of conditions or states of stock and other markets, individual or group stock price(s), commodity goods or services price(s), interest rates, foreign exchange rates, and property prices.

24. A monitoring device adapted to activate the stimulus device of the system of claim 12.

* * * * *